United States Patent [19]
Tantram

[11] Patent Number: 4,815,316
[45] Date of Patent: Mar. 28, 1989

[54] DIFFUSION MEASUREMENT

[75] Inventor: Anthony D. S. Tantram, Great Bookham, United Kingdom

[73] Assignee: City Technology Limited, United Kingdom

[21] Appl. No.: 116,148

[22] Filed: Nov. 3, 1987

[30] Foreign Application Priority Data

Nov. 5, 1986 [GB] United Kingdom ............... 8626430

[51] Int. Cl.⁴ .......................................... G01N 15/08
[52] U.S. Cl. ....................................................... 73/38
[58] Field of Search ............................................ 73/38

[56] References Cited

U.S. PATENT DOCUMENTS

| | | | |
|---|---|---|---|
| 3,286,509 | 11/1966 | Gluckman et al. | 73/38 |
| 3,590,634 | 7/1971 | Pasternak et al. | 73/38 X |
| 3,604,246 | 9/1971 | Toren | 73/38 |

Primary Examiner—Stewart J. Levy
Assistant Examiner—Joseph W. Roskos
Attorney, Agent, or Firm—Stevens, Davis, Miller & Mosher

[57] ABSTRACT

The diffusibility or permeability of a sample of material (6) is determined by mounting the sample in the wall of a chamber (1), having an electrochemical gas sensor (4) fitted therein. If a differential pressure is applied across the sample, and output signals from the gas sensor are recorded at least two times, the signals and times can be processed to yield diffusibility or permeability values.

10 Claims, 1 Drawing Sheet

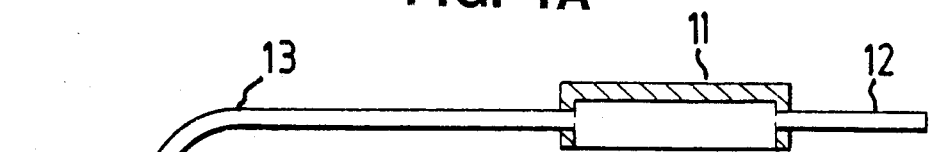
FIG. 1A
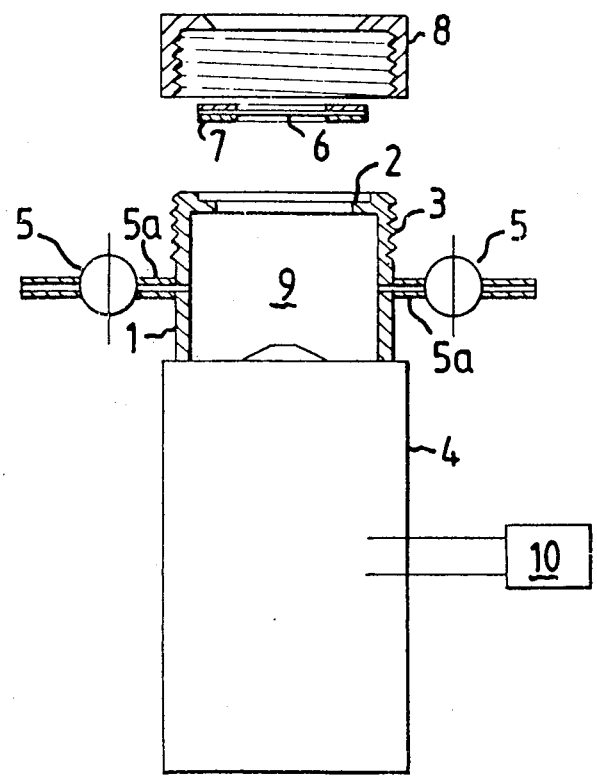

DIFFUSION MEASUREMENT

The present invention concerns diffusion measurement, and more especially it concerns the measurement of the diffusibility and/or permeability of porous materials.

Porous materials exhibit different gas transport mechanisms according to their pore size. If the pores in the material are larger than the mean free path of the gas molecule, the material can exhibit intermolecular diffusion resulting from any difference in partial pressure across the material, and bulk flow, resulting from a difference in total pressure. Intermolecular diffusion rates are independent of pore size and the material diffusibility is a measure of its ability to exhibit intermolecular diffusion. It is often difficult to measure diffusibility (also known as diffusivity), because of the tendency for bulk flow to obtrude. The ability of the material to exhibit bulk flow is its permeability, which for a given porosity, is proportional to the square of the pore diameter.

If the material pores are smaller than the mean free path of the gas molecule, the only diffusion mechanism is Knudsen diffusion, in which the molecules bounce off the pore walls and intermolecular collisions are insignificant. The rate of diffusion is proportional to the pore diameter.

It is an aim of the present invention to provide a simple and quick method of measuring diffusibility and/or permeability of porous materials. It is also an aim of the invention to provide a method of measuring the permeability of non-porous materials such as plastics films, in which the transport mechanism involves solution of the gas in the plastics material, diffusion of the gas in solution through the material, and escape from solution. It is possible from the diffusibility and/or permeability values for a porous material and obtained using one gas, to calculate values for other gases with acceptable accuracy. However, because of the varying solubility of gases in plastics materials, it is not possible to calculate permeability values from measurements on a single gas, for non-porous films.

It is to be appreciated that in the cases where only a single gas transport mechanism applies, the terms diffusibility and permeability are effectively synonomous.

It will be clear from theforegoing that when measuring diffusibilty we are concerned with the rate of transport due solely to a partial pressure difference across the sample, in the absence of any difference in total pressure (ie there is a difference in composition by volume on each side of the sample). When measuring permeability, we are concerned with the rate of gas transport due to a total pressure difference across the sample, the gas on each side of the sample now being of the same composition by volume.

Hereinafter, 'pressure difference' is used as a generic term and it should be understood that pressure difference always means partial pressure difference in a diffusibility measurement and total pressure difference in a permeability measurement, for porous materials. For non-porous materials, either a partial pressure difference or a total pressure difference may be used.

Previous methods normally employed a purge gas to carry away the gas diffusing or permeating through the sample under test, for external analysis. This has the disadvantage that the purge rate must also be accurately known. Furthermore, for measurement of diffusibility of porous bodies, it is essential that there be no total pressure difference across the sample, or bulk flow will interfere, and this is very difficult to achieve in a purge system. It is an aim of the invention to not only overcome these disadvantages, but also to provide a method and apparatus that allows a simple and rapid determination applicable to the measurement of either diffusibility or permeability, and without the need to calibrate the apparatus with a gas mixture of known concentration.

The present invention provides a method for determining the diffusibility and/or permeability of a material, comprising mounting a sample of the material in the wall of a chamber containing an electrochemical gas sensor capable of producing an output signal proportional to the concentration of a first (active) gas in an inert carrier gas, applying a pressure difference across the sample and then determining at least a first output signal from the sensor at a first time and a second output signal at a second time, and processing said signals and times to obtain a value for the diffusibility and/or permeability of the sample.

It will be appreciated that the rate of increase of the amount of the first (active) gas in the chamber will be a function of the volume of the chamber and the diffusibility or permeability of the sample as the case may be. The relationship will be discussed in more detail below.

The invention also provides an apparatus for the method of the invention, comprising a chamber having fitted therein an electrochemical gas sensor capable of producing an output signal proportional to the concentration of a first (active) gas in a carrier gas, means for mounting a sample of material in a wall of the chamber and means for applying a pressure difference across the sample. Preferably, the apparatus also comprises means for determining an output signal from the electrochemical gas sensor, means for time measurement and means for processing output signals and times to determine a value for diffusibility and/or permeability.

An electrochemical gas sensor that measures concentration on a partial pressure basis is generally preferred, and is required for permeability determination. For diffusibility determination, an electrochemical gas sensor measuring on a percent, or volume per basis, may, however, be used. There are many electrochemical gas sensors commercially available which possess suitable characteristics for use in the present invention. It is most convenient to measure oxygen as the active gas, as described hereafter, and suitable oxygen sensors are commercially available, although other active gases may be used with the appropriate sensors.

If the sensor is one that in operation consumes the active gas, then its sensitivity should be chosen to be low enough so that its specific rate of consumption in $cm^3$/second/atmosphere is negligible in relation to the diffusibility or permeability being measured, since, although its comsumption can in principle be corrected for, such a correction undesirably complicates the calculations.

The chamber may be made of any suitable material, provided only that it is inert to the gases used. It will be seen from the formula given below that the response time of the system will be proportional to the volume of the chamber and inversely proportional to the diffusibility or permeability, and these factors can be taken into account in selecting a suitable chamber volume, which is desirably from 0.5 to 100 $cm^3$, especially from 1 to 10 $cm^3$. Conveniently, the chamber has a cylindrical shape, desirably with a height similar to, or less than, its diameter. Preferably, the sample is mounted centrally at one end of the cylindrical chamber, with the sensor centrally mounted at the other end. The sensor is desirably removably fitted in the chamber, to permit replacement of an exhausted sensor, or replacment with a different type of sensor.

The method of the invention may be carried out in a matter of minutes after the sample is mounted in the apparatus.

The present invention will be further described by way of example only, with reference to the accompanying schematic drawing of one embodiment of an apparatus according to the invention.

BRIEF DESCRIPTION OF THE DRAWINGS

FIG. 1A is a schematic elevational view, partly in section, of a pressurizing water bubbler and outlet pipe with hood;

FIG. 1B is an elevational view in section of a threaded cap for sample holding and a sample to be tested; and FIG. 1C is an elevational view, partly in section, of an oxygen sensor with a threaded flange for connection to the sample holding cap.

Since air is readily available, measurements involving air are the simplest to make, and thus the following description will refer to the first (active) gas being oxygen, and the inert carrier gas being nitrogen.

Referring to the drawing, a cylinder, 1, having a flange, 2, and an externally threaded portion, 3, is sealed on to a commercial oxygen sensor, 4. The cylinder has inlet and outlet stopcocks, 5, connected to the cylinder by capillary tubes, 5a. The sample under test, 6, is mounted between two thin adhesive annular supports, 7, of impermeable material, and these define the sample test area. An internally threaded cap, 8, acts as a clamp to seal the sample and the supports onto the flange, and to form a chamber, 9. Leads from the sensor are taken to a signal measuring and display means, 10, of known type.

For the measurement of diffusibility, the chamber is purged with nitrogen, with the stopcocks 5 open. The inlet and outlet stopcocks are then opened in that order, so that the chamber is "sealed" at ambient pressure. Oxygen from the air outside will now start to diffuse into the chamber through the sample, resulting in an increasing signal from the oxygen sensor, and appropriate signal and time measurements are taken for the calculation of diffusibility, as discusssed below.

For the measurement of permeability, the chamber is purged with air, and at the point in time when the chamber is sealed as described above, air at a higher total pressure is applied to the outer face of the sample. A simple way of doing this is also illustrated in the FIG.; an additional hood, 11, has an air supply to its inlet pipe, 12. An outlet pipe, 13, is connected to a water bubbler, 14, the head of water being used to set the pressure. At the point in time when the chamber is sealed as described above, the hood 11 is mated to the cap 8. A differential pressure will then be applied across the sample determined by the head of water, h, as indicated in the FIG. As with diffusibility measurement, appropriate signal and time measurements are taken for the calculation of permeability.

We have found the same general equation may be used for calculating both diffusibility and permeability:

$$K = \frac{V}{(t_2 - t_1) P} \ln \frac{(S_a - S_1)}{(S_a - S_2)}$$

where
  K is the diffusibility or permeability as the case may be, and is in cm$^3$/sec/atm pressure difference (partial pressure difference for diffusibility, total pressure difference for permeability),
  P is the reference pressure in atm. at which the gas volume contained in K applies. This will normally be taken as 1 atm (P=1).
  V is the volume of the chamber in cm$^3$.
  $S_a$ is the "end" value of the sensor signal; ie for diffusibility determinations,
  $S_a$ will be the signal in ambient air. For the determination of permeability,
  $S_a$ will be the signal in air at the total externally applied pressure, ie
  (1+h) atm, where the head of water, h, is expressed in atm.
  $S_1$ is the sensor signal at the first time ($t_1$)
  $S_2$ is the sensor signal at the second time ($t_2$)

Since the sensor signals appear in the above formula as a ratio, they may be expressed in any suitable units.

Times are measured in seconds.

By way of simple example, the sensor may be calibrated so that $S_a$=100 units, the first time ($t_1$) recorded when $S_1$=5, and the second time recorded when $S_2$=55. With P=1, $$K = \frac{V}{(t_2 - t_1)} \ln \frac{95}{45} = \frac{0.747 V}{(t_2 - t_1)}$$

The signal processing may be done in a variety of ways. Time measurement may be done using a stopwatch, and signals read from a meter or other display device, with the calculations being performed on a calculator. A dedicated microprocessor or a suitably programmed microcomputer may be used to count time, to record signals and to calculate and display on a screen, printout etc, a value for diffusibility or permeability as the case may be.

While only two values of each of S and t are necessary to calculate K, it will be appreciated that, particularly if a dedicated microprocessor or a suitably programmed computer is used, a large number of values of S and t may be used to calculate K on the basis of the formula given, to achieve a higher accuracy than the simple two point method.

A problem can arise with the measurement of very diffusible materials, when the stagnant layer of gas on either side of the sample within the confines of its mount may present a relatively significant diffusion resistance. It has been found that this problem can be readily overcome by means of a blank measurement. That is, a diffusibility measurement as described, with the mount in position but no sample present. If $K_b$ is the blank diffusibility, and $K_m$ the diffusibility measured with the sample in position, then the true diffusibility of the sample, $K_s$, will be given by the forumla:

$$K_s = \frac{K_b K_m}{K_b - K_m}$$

When the two point method of calculation is used, the blank time interval $\Delta t_b$ may simply be subtracted from the measured time interval $\Delta t_m$ to give $\Delta t_s$, and $\Delta t_s$ used in the calculation will give the true diffusibility of the sample, $K_s$.

When measuring permeability, it is not necessary to do a blank correction, since the blank permeability resistance will be insignificant.

The value of K refers to the available area of sample used and to the actual thickness of sample used. These parameters should be measured in order to compute a more general value referring to unit area and unit thickness. The value of K will also be specific to the temperature applying at the time of the measurement.

I claim:

1. A method for determining the diffusibility and/or permeability of a material, comprising
    mounting a sample of the material in the wall of a chamber containing an electrochemical gas sensor capable of producing an output signal proportional to the concentration of a first (active) gas in an inert carrier gas,
    applying a pressure difference of said first gas across the sample and then determining at least a first output signal from the sensor at a first time corresponding to a first concentration in the chamber of siad first gas,
    and subsequently determining a second output signal from the sensor at a second time corresponding to a second concentration of said first gas in the chamber,
    and processing said signals and times to obtain a value for the diffusibility and/or permeability of the sample.

2. The method of claim 1, wherein the sensor produces an output signal proportional to the partial pressure of the first gas in the inert gas.

3. The method of claim 1, wherein the first gas in the oxygen in air.

4. The method of claim 1, wherein a dedicated microprocessor or programmed microcomputer is used to measure time, record said at least first and second output signals from the sensor, and to calculate and display a value for the diffusibilty and/or permeability of the sample.

5. An apparatus for determining the diffusibility and/or permeability of a sample of material, said apparatus comprising a chamber having fitted therein an electrochemical gas sensor capable of producing an output signal proportional to the concentration of a first (active) gas in an inert carrier gas, means for mounting the sample in a wall of the chamber, and means for appying a pressure difference across the sample.

6. The apparatus of claim 5, comprising also means for time measurement.

7. The apparatus of claim 5, comprising also means for processing output signals from the sensor and times to obtain a value for diffusibility and/or permeability.

8. The apparatus of claim 5, wherein the sensor is an oxygen sensor.

9. The apparatus of claim 5, wherein the chamber is cylindrical with a height not greater than its diameter.

10. The apparatus of claim 9, wherein the sample is mounted centrally at one end of the cylindrical chamber, and the sensor is fitted centrally at the other end of the chamber.

* * * * *